US008642064B2

(12) United States Patent
Schnabelrauch et al.

(10) Patent No.: US 8,642,064 B2
(45) Date of Patent: Feb. 4, 2014

(54) BIOABSORBABLE COMPOSITE MATERIAL

(75) Inventors: Matthias Schnabelrauch, Jena (DE); Sebastian Vogt, Erfurt (DE); Dieter Reif, Altendambach (DE); Ute (Erbe) Reif, legal representative, Altendambach (DE)

(73) Assignee: Curasan AG, Frankfurt am Main (DE)

( * ) Notice: Subject to any disclaimer, the term of this patent is extended or adjusted under 35 U.S.C. 154(b) by 1545 days.

(21) Appl. No.: 10/580,549

(22) PCT Filed: Nov. 25, 2004

(86) PCT No.: PCT/EP2004/013388
§ 371 (c)(1),
(2), (4) Date: Apr. 3, 2007

(87) PCT Pub. No.: WO2005/051443
PCT Pub. Date: Jun. 9, 2005

(65) Prior Publication Data
US 2007/0254011 A1  Nov. 1, 2007

(30) Foreign Application Priority Data
Nov. 27, 2003  (DE) ................................. 103 55 992

(51) Int. Cl.
*A61F 2/00* (2006.01)
*A61F 13/00* (2006.01)
*C09K 3/00* (2006.01)

(52) U.S. Cl.
USPC ........... 424/426; 424/422; 424/423; 523/113; 523/115; 523/116; 106/35

(58) Field of Classification Search
None
See application file for complete search history.

(56) References Cited

U.S. PATENT DOCUMENTS

| 4,192,021 A * | 3/1980 | Deibig et al. ............. 623/23.61 |
| 4,373,217 A * | 2/1983 | Draenert .................. 623/23.62 |
| 5,650,108 A | 7/1997 | Nies et al. |
| 5,814,681 A | 9/1998 | Hino et al. |
| 6,281,271 B1 | 8/2001 | Rumphorst et al. |
| 6,340,648 B1 | 1/2002 | Imura et al. |
| 2002/0120033 A1 | 8/2002 | Jia et al. |

FOREIGN PATENT DOCUMENTS

| DE | 199 39 403 | | 2/2001 | |
| DE | 199 39 403 A1 * | | 2/2001 | ............. C08L 33/00 |
| WO | WO 87/00058 | | 1/1987 | |

OTHER PUBLICATIONS

Machine translation for DE 199 39 403 A1 (attached as NPL).*
Merriam-Webster Online Dictionary: "prophylaxis" (http://www.merriam-webster.com/dictionary/prophylaxis) and "prevent" (http://www.merriam-webster.com/dictionary/prevent).*
http://en.wikipedia.org/wiki/Chlorophyll.*
"BET" surface area (http://en.wikipedia.org/wiki/BET_theory).*

* cited by examiner

Primary Examiner — Robert A Wax
Assistant Examiner — Jeffrey T Palenik
(74) Attorney, Agent, or Firm — Roylance, Abrams, Berdo & Goodman, L.L.P.

(57) ABSTRACT

A method of producing a self-hardening, bioabsorbable composite material, the material produced and its areas of application are described. The method is based on the principal method steps (I) immobilisation of a polymerisation initiator in a microporous pore system of a first partial amount of a bioabsorbable calcium phosphate used in producing the self-hardening, bioabsorbable composite material, (II) immobilisation of a polymerisation activator in the microporous pore system of a second partial amount of the bioabsorbable calcium phosphate used in producing the self-hardening, bioabsorbable composite material and (III) homogeneous mixing of the components according to (I) and (II) with a liquid or paste-form, multi-functional monomer capable of forming a biocompatible, bioabsorbable polymer network or a corresponding monomer mixture and, optionally, with further constituents which modify the properties of the monomer or monomer mixture. The described self-hardening, bioabsorbable composite materials can be used as bone adhesives for the fixing of bone fractures, as shaped pieces of standardised dimensions and as implants that are individual to a patient in the context of regenerative bone healing in humans and animals.

32 Claims, No Drawings

BIOABSORBABLE COMPOSITE MATERIAL

FIELD OF THE INVENTION

The present invention relates to a method of producing a self-hardening, bioabsorbable composite material, to a self-hardening, bioabsorbable composite material and to the use thereof in human and veterinary medicine, especially for bonding bone tissue, for filling bone defects and for producing implantable shaped pieces.

BACKGROUND OF THE INVENTION

Non-absorbable, or just partially absorbable, bone cements have been known for a long time and have been described in a large number of patents and scientific publications (e.g. G. Lewis, J. Biomed. Mater. Res. (Appl. Biomater.) 38 (1997) 155). They usually consist of a liquid component and a solid component. The liquid component consists of a liquid monofunctional methacrylic acid ester, with preference being given to the use of methyl methacrylate. A polymerisation activator, usually N,N-dimethyl-p-toluidine, is dissolved in that monomer. The solid component consists of a polymer which is swellable or soluble in the monomer, with copolymers of methyl methacrylate and of methylacrylate being most frequently used. Contained in the solid component is a polymerisation initiator, such as dibenzoyl peroxide. Curing of those bone cements is accomplished by means of the fact that the polymerisation activator dissolved in the monomer comes into contact with the polymerisation initiator contained in the solid component. As a result of. the action of the polymerisation activator, the polymerisation initiator decomposes immediately, giving rise to free radicals which immediately trigger polymerisation of the monofunctional monomer. As a result of polymerisation of the monofunctional monomers there are formed non-crosslinked polymers which are soluble or swellable in the as yet unreacted monomer. As a result, for a period of several minutes, the cement remains plastically deformable and can be worked. The polymerisation speed is dependent only on the initiator and monomer concentrations and therefore is relatively slow.

In the case of multi-functional monomers, those bone cements are no longer feasible because multi-functional monomers, by virtue of their polymerisation kinetics, polymerise extremely quickly and result in solid polymer networks which, even in the case of low degrees of crosslinking, can no longer be plastically deformed and therefore worked.

In U.S. Pat. No. 5,814,682 there is described a composition formed by a paste A, which consists of a mixture of a polymerisable monomer, an initiator and calcium phosphate, and a paste B, which consists of a mixture of a polymerisable monomer, an activator and calcium phosphate. After pastes A and B have been mixed together, the composition polymerises.

A composite system similar to U.S. Pat. No. 5,814,682 is described in WO 87100058. A bone cement based on diacrylate or dimethacrylate comprises absorbable particles of bioceramic material or bioglass. The inorganic filler particles should have a pore volume of at least 0.2 ml/g because this is said to have a beneficial effect on the physical properties of the cement.

A dental material capable of free radical polymerisation has been described in EP 0951896 A2. That dental material is characterised in that the filler is formed by a homogeneous mixture of a first part of the filler, which is coated with the polymerisation initiator, a second part of the filler, which is coated with the polymerisation activator, and a third part of the filler, which does not comprise any component of the initiator system.

A biologically degradable composite material is disclosed in DE 19939403 A1. The composite material is formed by curing of the mixture of a liquid component A, which comprises at least one polymerisable, bioabsorbable monomer and, optionally, a bioabsorbable thickener, a solid component B, which consists of a bioabsorbable inorganic filler coated with a polymerisation initiator, and a solid component C, which is formed by a bioabsorbable inorganic filler coated with a polymerisation activator. In that composite system, the polymerisation activator and the polymerisation initiator are applied as coatings to the surface of fillers. The inorganic filler may be calcium carbonate, magnesium carbonate, calcium phosphate or hydroxyapatite; there is no requirement for interconnecting porosity.

DE 198 18 210 A1 describes a dental material capable of free radical polymerisation, having at least one polymerisable binder and at least one filler and comprising a redox initiator system for the free radical polymerisation, the system comprising an initiator and an activator. In the known material, the filler is a homogeneous mixture of a first part of the filler, which is mixed with the initiator, a second part of the filler, which is mixed with the activator, and a third part of the filler, which does not comprise any component of the initiator system. Again, interconnecting porosity is not required for the filler, with mention being made of, for example, quartz powder, glass-ceramic powder, glass powder, aluminium powder and silicon dioxide powder as preferred fillers.

U.S. Pat. No. 5,814,681 relates to a restorative composition for hard tissue, comprising inorganic calcium phosphate powder; again, there is no requirement for interconnecting porosity. $\omega,\omega'$-unsaturated compounds are provided as polymerisable monomers, the following warning being given for the polymerisation thereof:

"Excess time for mixing leads to the initiation of curing before application of the mixture to the affected part, thereby making the mixture unavailable."

DE 44 35 860 A1 relates to production of a porous bone replacement material using an inorganic starting material, the porosity of which is not specified. For production of the known bone replacement material, a mixture of (a) a polymerisation product comprising polymerisation catalyst, (b) a liquid monomer comprising polymerisation accelerator and (c) inorganic material in the form of coarsely particulate granules is used as starting material.

DE 100 18 394 A1 relates to production of porous calcium phosphate pieces obtained by sintering.

SUMMARY OF THE INVENTION

The prior art of self-hardening, bioabsorbable composite materials is consequently characterised in that the polymerisation activators and polymerisation initiators required for crosslinking of the monomers are mixed in with the various components of the composite system or applied to the surface of those components. The present invention is accordingly based on the problem of being able to achieve even better control of the reaction of those accelerator components in the case of multi-functional monomers.

DETAILED DESCRIPTION OF THE INVENTION

The invention is furthermore based on the problem of providing a new, self-hardening, bioabsorbable composite material on the basis of di-, tri- or other multi-functional monomers as polymer network formers. It should be possible for that composite material to be made by mixing together individual composite constituents and/or previously produced partial mixtures or partial reaction products so as to form a pourable, injectable or spreadable mass and to cure automatically at room temperature after a processing time of from 2 to 5 minutes to form a solid composite.

The problem on which the invention is based is now solved, in accordance with one embodiment, by a method of producing a self-hardening, bioabsorbable composite material, wherein (i) a polymerisation initiator is immobilised with the aid of a first partial amount of an interconnectingly porous bioabsorbable inorganic bone regeneration material,
(ii) a polymerisation activator is immobilised with the aid of a second partial amount of the bone regeneration material according to (i) or of a different interconnectingly porous bioabsorbable inorganic bone regeneration material,
(iii) the components obtained in steps (i) and (ii) are mixed with a liquid or paste-form multi-functional monomer capable of polymerisation to form a biocompatible and bioabsorbable polymer or with a liquid or paste-form mixture of multi-functional monomers capable of polymerisation to form a biocompatible and bioabsorbable polymer, and
(iv) the monomer or monomer mixture contained in the mixture produced is polymerised to form the polymer and the composite material is obtained.

The problem is accordingly solved, in accordance with the invention, by provision of a new method of producing a self-hardening, bioabsorbable composite material which comprises three basic method steps. In the process it was found, surprisingly, that by means of calcium phosphates having an interconnecting pore system or an interconnectingly porous system, for example a microporous pore system, polymerisation initiators and polymerisation activators can be so immobilised that liquid or paste-form monomers do not elute them from the pore system immediately but rather over an extended period.

That immobilisation effect can be further increased, for example, when the initiator and activator, after having been immobilised using the particle-form, particulate or granular porous calcium phosphate, are dissolved away from the surfaces or outsides of the particles and allowed to remain solely inside pores, before adding the monomer.

Partial dissolution of such a kind can be promoted, for example, by wetting with a solvent for just a short time and/or by not allowing the solvent to penetrate into the pores, for example by not evacuating the pores.

In the method according to the invention, especially in step (iii), constituents which modify the properties of the monomer, monomer mixture and/or composite material may be mixed in.

Accordingly, in the method according to the invention, especially in step (iii), constituents which modify the properties of the monomer, monomer mixture and/or composite material may be mixed in. Such constituents may be, for example, substances which alter the viscosity of the monomer, the monomer mixture and/or the mixture thereof with the bone regeneration material in a manner that is desirable for application. Further such constituents which may be mixed in may be substances that alter the pH, pore-formers (so-called porogens), adhesion-imparting agents, colourants, contrast agents and/or pharmaceutical active ingredients.

There may accordingly be mixed in one or more modifying constituents selected from the group: thickeners, diluents, polymeric fillers, porogens, pH-modifying substances, colourants and adhesion-imparting agents.

Furthermore, in the method according to the invention, the first partial amount and the second partial amount of the bone regeneration material may be used in a ratio of from 1:10 to 10:1 and/or the polymerisation initiator and the polymerisation activator may be immobilised with and/or in the respective partial amounts of the bone regeneration material in a ratio of from 1:10 to 10:1 (based on weight in each case).

Furthermore, in the method according to the invention, the bone regeneration material may be used in the form of powder or granules.

Furthermore, in the method according to the invention, in step (i), a solution of the polymerisation initiator may be added to the bone regeneration material, the solution allowed to infiltrate the bone regeneration material and afterwards the bone regeneration material dried.

Furthermore, in the method according to the invention, a solution of the polymerisation initiator may be mixed with the amount (partial amount) of bone regeneration material, provided for the immobilisation thereof, in an amount of from 0.1 to 20% by weight (solid initiator based on bone regeneration material).

Furthermore, in the method according to the invention, an organic peroxide may be used as polymerisation initiator, preferably an organic peroxide selected from the group comprising dibenzoyl peroxide, lauroyl peroxide and acetone peroxide.

Furthermore, in the method according to the invention, in step (ii), a melt or a solution of the polymerisation activator may be added to the bone regeneration material, the melt or the solution allowed to infiltrate the bone regeneration material and afterwards the bone regeneration material dried.

Furthermore, in the method according to the invention, a solution of the polymerisation activator may be mixed with the amount (partial amount) of bone regeneration material provided for the immobilisation thereof in an amount of from 0.1 to 20% by weight (solid activator based on bone regeneration material).

Furthermore, in the method according to the invention, one or more polymerisation activators may be used which are selected from the group comprising N,N-bis(2-hydroxyethyl)-p-toluidine, N,N-dimethyl-p-toluidine, N,N-dimethyl-N,N-aniline, ascorbic acid and barbituric acid.

Furthermore, in the method according to the invention, the polymerisation initiator may be used in the form of a solution and/or the polymerisation activator may be used in the form of a solution and the solution(s) allowed to be drawn up by the bone regeneration material completely or as far as possible and the excess not drawn up removed before step (iii).

Furthermore, in the method according to the invention, there may be used, as inorganic bone regeneration material, an alkaline earth metal phosphate and/or an alkali metal/alkaline earth metal phosphate, especially an alkaline earth metal orthophosphate and/or alkali metal/alkaline earth metal orthophosphate, preferably a bone regeneration material which is selected from the group comprising alpha-tricalcium phosphate, beta-tricalcium phosphate, calcium-deficient carbonate-containing hydroxyapatite, octacalcium phosphate, magnesium phosphate, calcium hydrogen phosphate, calcium/sodium orthophosphate and calcium pyrophosphate.

Furthermore, in the method according to the invention, for immobilisation of the polymerisation initiator there may be used a bone regeneration material which is the same as or different from that for immobilisation of the polymerisation activator. That free choice corresponds in that respect to the prior art, for example according to U.S. Pat. No. 5,814,681 column 3 lines 53-55.

In that case, the bone regeneration material for immobilisation of the initiator may differ from the bone regeneration material for immobilisation of the activator in its chemical and/or mineralogical nature.

Furthermore, in the method according to the invention, an interconnectingly porous bone regeneration material, especially calcium phosphate, having the following characteristic data may be used:

pore diameters from 0.1 to 500 μm, preferably from 0.1 to 100 μm and especially from 0.1 to 10 μm, and/or particle sizes ($d_{50}$ values) of from 1 to 500 μm, preferably from 5 to 300 μm, and/or BET surface area of at least 0.1 $m^2/g$.

Furthermore, in the method according to the invention, there may be used an interconnectingly porous bone regeneration material, especially calcium phosphate, having a pore volume, accessible to the polymerisation initiator and/or the polymerisation activator, of 0.4 $cm^3/g$ or more, and especially from 0.4 to 3.3 $cm^3/g$, while retaining the integrity of the particles of the bone regeneration material.

Furthermore, in the method according to the invention, the bone regeneration material, especially calcium phosphate, may be used in crystalline, partly crystalline, glassy or amorphous form.

Furthermore, in the method according to the invention, constituents which are biocompatible and which modify the properties of the regeneration material, especially silicon compounds, may be mixed in with the bone regeneration material.

Furthermore, in the method according to the invention, as the monomer or as monomers of the monomer mixture there may be used a multi-functional oligomer having terminal methacrylate groups, especially an oligomer of lactic acid and/or glycolic acid and/or delta-hydroxyvaleric acid and/or epsilon-hydroxycaproic acid and/or trimethylene carbonate.

In that case, the monomer or monomer mixture may be used together with an adhesion-imparting agent, preferably a hydroxyl-group-containing adhesion-imparting agent, especially methacrylic acid 2-hydroxyethyl ester.

Furthermore, in the method according to the invention, the monomer or monomer mixture may be used together with a viscosity-modifying substance or thickener, preferably dianhydro-D-glucitol-bis(poly-D,L-lactide).

In accordance with a further embodiment, the problem on which the invention is based is solved by a self-hardened bioabsorbable composite material which can be produced by
(i) immobilising a polymerisation initiator with the aid of a first partial amount of the bone regeneration material according to (i) or a different interconnectingly porous bioabsorbable inorganic bone regeneration material,
(ii) immobilising a polymerisation activator with the aid of a second partial amount of the bone regeneration material according to (i) or of a different interconnectingly porous bioabsorbable inorganic bone regeneration material,
(iii) mixing the components obtained in steps (i) and (ii) with a liquid or paste-form multi-functional monomer capable of polymerisation to form a biocompatible and bioabsorbable polymer or with a liquid or paste-form mixture of multi-functional monomers capable of polymerisation to form a biocompatible and bioabsorbable polymer, and
(iv) polymerising the monomer or monomer mixture contained in the mixture produced, to form the polymer, and obtaining the composite material.

In the composite material, the weight ratio of bone regeneration material: monomer or monomer mixture may be from 4:6 to 8:2.

The composite material according to the invention may be obtainable by a method according to the invention.

In accordance with a further embodiment, the problem on which the invention is based is solved by a self-hardening bioabsorbable composite material in the form of a set consisting of or comprising
(i) a first partial amount of an interconnectingly porous bioabsorbable inorganic bone regeneration material and a polymerisation initiator which is immobilised with the aid that first partial amount,
(ii) a second partial amount of the bone regeneration material according to (i) or of a different interconnectingly porous bioabsorbable inorganic bone regeneration material and a polymerisation activator which is immobilised with the aid of that second partial amount, and
(iii) a liquid or paste-form multi-functional monomer capable of polymerisation to form a biocompatible and bioabsorbable polymer or a liquid or paste-form mixture of multi-functional monomers capable of polymerisation to form a biocompatible and bioabsorbable polymer.

In the composite material according to the invention, the weight ratio of bone regeneration material: monomer or monomer mixture may be from 4:6 to 7:3.

The composite material according to the invention may be obtainable in the form of a set by the method according to the invention, in the same manner as each of its components (i), (ii) and (iii).

In accordance with a further embodiment, the problem on which the invention is based is solved by use of a self-hardened composite material according to the invention in machine-production of implants in the form of shaped pieces of standardised dimensions for bone regeneration or of implants that are individual to a patient.

The problem on which the invention is based is solved, finally, by use of a self-hardening bone regeneration material in the form of a set according to the invention in producing a bone adhesive for the fixing of bone fractures.

In accordance with the invention, in a first partial step (I), a polymerisation initiator is accordingly immobilised in an interconnecting pore system of a first partial amount of a bioabsorbable bone regeneration material, for example a calcium phosphate, used in producing the self-hardening, bioabsorbable composite material. In a further method step (II), a polymerisation activator is immobilised in the interconnecting pore system of a second partial amount of the bioabsorbable bone regeneration material, for example a calcium phosphate, used in producing the self-hardening, bioabsorbable composite material. In that case, the first partial amount and the second partial amount are in a ratio of from 1:10 to 10:1, and the polymerisation initiator and the polymerisation activator are in a ratio of from 1:10 to 10:1 (based on weight in each case). In a third method step (III), the components according to (I) and (II) are homogeneously mixed with a liquid or paste-form monomer or monomer mixture capable of forming a biocompatible, bioabsorbable polymer network and, optionally, further constituents which modify the properties of the monomer. Such property-modifying constituents may be, for example, substances which alter the viscosity of the monomer, monomer mixture and/or the mixture thereof with the bone regeneration material in a manner that is desirable for application. Further such constituents which may be mixed in may be pH-modifying substances, pore-formers (so-called porogens), adhesion-imparting agents, colourants, contrast agents and/or pharmaceutical active ingredients. For the amount of monomer or monomer mixture and of modifying constituents, reference may be made to the prior art.

In the context of the present invention, immobilisation is understood to be, preferably, the temporary fixing of a reaction-accelerating substance in the interconnecting pore or channel system of suitable carrier particles, which are themselves substantially non-reactive, of bone regeneration material, e.g. calcium phosphate. With regard to the size of the carrier particles, reference may be made to the prior art. In principle, in the context of the new method, it is also possible to envisage the application of further principles involving delayed active ingredient release which are known from drug delivery systems; cf., for example, Schmidt et al. in J. Controlled Release, 37 (1995) 83-94 and Cimbollek et al. in Antimicrob. Agents Chemother., 40 (1996) 1432-1437. The decisive factor for suitability for use is a release rate which is appropriate to solving the problem according to the invention.

When such interconnectingly porous bone regeneration materials, e.g. calcium phosphates, in which at least one polymerisation initiator is immobilised, and such interconnectingly porous bone regeneration materials, e.g. calcium phosphates, in which at least one polymerisation activator is immobilised, are mixed with liquid or paste-form multi-functional polymer-network-forming monomers or monomer mixtures, the resulting mixtures are, surprisingly, capable of being worked at room temperature over a period of from 2 to 10 minutes. During that time, the mixtures are plastically deformable and injectable, pourable and spreadable. After that, curing occurs suddenly.

On the basis of the polymerisation kinetics, known per se, of multi-functional monomers, this finding is surprising. With the known polymerisation kinetics one would expect a processing time of a few seconds.

It may be assumed that the processing time of the self-hardening, bioabsorbable composite material is governed by delayed diffusion out of the pore systems of the porous bone regeneration materials such as, for example, calcium phosphates. It is furthermore assumed that the pore diameter and channel diameter of the interconnecting pore system and the size of the interconnecting pore systems have an influence on the diffusion, governed by the particle size distribution of the bioabsorbable bone regeneration materials such as, for example, calcium phosphates. The diffusion rate is additionally influenced by temperature.

In the context of the present invention, bone regeneration material is understood to be any bioabsorbable material, suitable for bone regeneration, from the group of the alkaline earth metal and alkali metal-alkaline earth metal phosphates, especially calcium phosphates. The specific material composition of the bioabsorbable bone regeneration material, e.g. calcium phosphate, is of subordinate importance for the self-hardening, bioabsorbable composite material according to the invention, in comparison to its internal surface and pore structure.

For its immobilisation, the polymerisation initiator in dissolved form is mixed with a first partial amount of the bioabsorbable regeneration material such as calcium phosphate in a relative amount of, for example, from 0.1 to 20% by weight and the concentration of its solution is so adjusted that the bone regeneration material draws up the solution of the polymerisation initiator into its interconnecting pore system completely. The bone regeneration material is then dried and so is available for further production steps, such as packaging and sterilisation. After the bone regeneration material soaked with the solution of the polymerisation initiator has been dried, the initiator fills the pore systems of the bone regeneration material entirely or at least partly.

As polymerisation initiator, materials from the group of organic peroxides, preferably dibenzoyl peroxide, lauroyl peroxide and/or acetone peroxide, have been found to be especially suitable. Solvents suitable for the polymerisation initiator are various ketones, preferably acetone. They are distinguished, on the one hand, by good dissolution characteristics and, on the other hand, by good drying characteristics and can be removed completely from the pore system of the bone regeneration material, for example the calcium phosphate, without impairing the reaction characteristics of the polymerisation initiator.

The polymerisation activator is immobilised in analogous manner, by dissolving it in an organic solvent or by melting it, and mixing it, for example in an amount of from 0.1 to 20% by weight based on a second partial amount of the bone regeneration material, e.g. calcium phosphate, with the latter. The concentration of the solution in that case is so adjusted that the latter is likewise drawn up into the pore system of the bone regeneration material completely. The bone regeneration material is then dried and is available for further production steps, such as packaging and sterilisation. After the bone regeneration material soaked with the solution of the polymerisation activator has been dried, the activator fills the pore systems of the bone regeneration material entirely or at least partly.

Suitable solvents are to be found, for example, in the prior art.

As polymerisation activator, materials from the group N,N-bis(2-hydroxyethyl)-p-toluidine, N,N-dimethyl-p-toluidine, N,N-dimethyl-N,N-aniline, ascorbic acid and barbituric acid alone or in admixture have been found to be suitable. Suitable solvents for the polymerisation activator are various alcohols or ketones, preferably ethanol. They are distinguished, on the one hand, by good dissolution characteristics and, on the other hand, by good drying characteristics and can be removed completely from the micropore system of the calcium phosphate without impairing the reaction characteristics of the polymerisation activator.

Suitable bone regeneration materials such as, for example, calcium phosphates are bioabsorbable materials that have been successfully used for bone regeneration from the group of alkaline earth metal phosphates and alkali metal-alkaline metal earth phosphates, especially their orthophosphates, such as alpha-tricalcium phosphate or beta-tricalcium phosphate, magnesium phosphate, calcium/sodium orthophosphate, calcium-deficient, carbonate-containing hydroxyapatite, octacalcium phosphate, calcium hydrogen phosphate and/or calcium pyrophosphate. The first partial amount of the bone regeneration material used for immobilisation of the polymerisation initiator may be chemically and mineralogically identical to the second partial amount for immobilisation of the polymerisation activator. However, the two partial amounts may also differ in their chemical or mineralogical nature if that does not have a negative effect but rather a beneficial effect on the properties of the self-hardening, bioabsorbable composite material.

The interconnecting pore system of the bioabsorbable bone regeneration materials, e.g. calcium phosphates, has pore cross-sections preferably in the range from 0.1 to 100 µm, more preferably in the range from 0.1 to 10 µm, the particle size distribution of the bioabsorbable bone regeneration materials having an effect on the release of the polymerisation initiator and the polymerisation activator such that, with increasing particle size, the speed of release and, as a result, the speed of polymerisation are slowed down. In accordance with the invention, particle sizes (as $d_{50}$ values) in a range from 1 to 500 µm, preferably from 5 to 300 µm, have been found to be suitable for the desired reaction times. The bone regeneration material, e.g. calcium phosphate, may be used in crystalline, glassy crystalline or amorphous form. For the task of immobilisation, the crystalline form of the material is of subordinate importance in comparison to the interconnecting pore structure and particle size distribution of the bone regeneration material particles.

The interconnecting pore structure of the bone regeneration material, e.g. calcium phosphate, advantageously has a high internal surface area with small pore/channel diameters. A preferred embodiment has a BET surface area of at least 0.1 $m^2/g$ with average pore diameters in the range from 0.1 to 20 µm.

Further biocompatible, property- and/or structure-modifying constituents, e.g. silicon compounds, may be added to the bone regeneration materials, e.g. calcium phosphates, for the purpose of modifying their properties.

The polymer content of the self-hardening, bioabsorbable composite material is produced from a liquid or paste-form monomer capable of forming a biocompatible, bioabsorbable polymer network or from a mixture of such monomers and by polymerisation thereof using the above-indicated polymerisation initiators and polymerisation activators. In accordance with the invention, the liquid or paste-form monomer or monomer mixture consists of a material from the group of multi-functional, methacrylate-terminated oligomers, preferably based on lactic acid and/or glycolic acid and/or δ-hydroxyvaleric acid and/or ε-hydroxy-caproic acid and/or trimethylene carbonate.

The self-hardening, bioabsorbable composite material is formed from 40 to 80% by weight of a bone regeneration material, e.g. calcium phosphate or calcium phosphate mixture, and from 20 to 60% by weight of a liquid or paste-form, bioabsorbable, multi-functional monomer or monomer mixture and, optionally, further constituents which modify the properties of the monomer. Its formulation consists of a mixture of at least a starting component A, consisting of an interconnectingly porous bone regeneration material, e.g. calcium phosphate, in the pore system of which a polymerisation initiator has been immobilised, a starting component B, consisting of an interconnectingly porous bone regeneration material, e.g. calcium phosphate, in the pore system of which a polymerisation activator has been immobilised, and a starting component C, consisting of a liquid or paste-form, bioabsorbable, multi-functional monomer or a corresponding monomer mixture and, optionally, further constituents which modify the properties of the monomer or monomer mixture.

Such property-modifying constituents are, for example, substances which alter the viscosity of the monomer, monomer mixture and/or the mixture thereof with the bone regeneration material in a manner that is desirable for processing and application. Examples of suitable viscosity-altering substances are oligomeric or polymeric derivatives of alpha-hydroxycarboxylic acids, especially of lactic and glycolic acid and also copolymers thereof and/or oligo- and poly-ethylene glycols. Dianhydro-D-glucitol-bis(poly-D,L-lactide) having a molecular weight of about 17,000 g/mol is an especially suitable viscosity-increasing substance. Further property-modifying constituents are substances which are water-soluble or which react with water to form water-soluble resultant products and which bring about a pH change in a water-containing medium, as a result of which the decomposition rate of the self-hardened composite material can be modified. Property-modifying constituents are also water-soluble substances which, in particulate form, are mixed in with the monomer, monomer mixture and/or mixture thereof with the bone regeneration material and which, after introduction of the self-hardened composite material into a water-containing medium, for example a bone defect, are dissolved out from the composite material, whereby additional pores are formed. By that means, the growth of cells into the absorbable composite material and degradation of the latter may be accelerated. As an especially suitable pore-former there may be used particulate sodium hydrogen carbonate. Further property-modifying constituents are adhesion-imparting agents, which improve the adhesion between the self-hardened composite material and the natural tissue, especially hard tissue. Suitable adhesion-imparting agents are especially those which have free hydroxyl groups, such as, for example, methacrylic acid 2-hydroxyethyl ester.

Property-modifying constituents are also colourants and/or contrast agents, which are used, for example, for facilitating visualisation of the composite material in the body. Further property-modifying constituents are pharmaceutical active ingredients or active ingredient mixtures which are released from the composite material after implantation and may be used for local therapeutic or prophylactic treatment of the tissue located in the vicinity of the composite material. Examples of active ingredients that may be mixed in are antibiotics, anti-inflammatories, proteinogenic growth factors or cancerostatics.

The self-hardening, bioabsorbable composite material is produced by polymerisation of a mixture of a starting component A, consisting of an interconnectingly porous bone regeneration material, e.g. calcium phosphate, in the pore system of which a polymerisation initiator has been immobilised, a starting component B, consisting of an interconnectingly porous bone regeneration material, e.g. calcium phosphate, in the pore system of which a polymerisation activator has been immobilised, and a starting component C, consisting of a liquid or paste-form, bioabsorbable, multi-functional monomer or a multi-functional monomer mixture. Optionally, further constituents which modify the properties of the monomer, of the monomer mixture or of the self-hardening, bioabsorbable composite material itself may be included.

The self-hardening, bioabsorbable composite material is formed from 40 to 80% by weight of bone regeneration material, e.g. calcium phosphate, and from 20 to 60% by weight of a liquid or paste-form, bioabsorbable, multi-functional monomer or a multi-functional monomer mixture and, optionally, further constituents which modify the properties of the monomer.

The self-hardening, bioabsorbable composite material is used in two different ways depending on the procedure used as part of bone healing. When in vivo polymerisation is used, use as a self-hardening, bioabsorbable bone adhesive is possible whereas, in the case of in vitro polymerisation, implants can be produced from compact pieces of composite by suitable processing methods.

The bioabsorbable bone adhesive is used preferably for the fixing of comminuted fractures in regions of the skeleton that are not loaded or that are subject to low loading and may, when combined with osteosynthesis measures, be used in the entire region of the skeleton.

Cured materials produced using the bone adhesive according to the invention, e.g. in the form of cylindrical pieces, are suitable for producing implants for bone regeneration. They may be machined very well and with a high degree of accuracy. It is possible to produce shaped pieces of standardised dimensions and also shaped pieces that are individual to a patient, which may be used as bioabsorbable implants as part of bone healing.

The Invention Is Explained Hereinbelow Using Examples

For producing the self-hardening, bioabsorbable composite material there are used three starting components A, B and C and, optionally, adhesion-imparting agents and thickeners suitable for improving the processing properties and/or the physical properties of the self-hardening, bioabsorbable composite material:

| | |
|---|---|
| Starting component A: | Pure-phase β-tricalcium phosphate, particle size <50 μm, 0.2 m$^2$/g BET surface area, 90% of the pores are in the diameter range 2 ± 1 μm and containing immobilised polymerisation initiator |
| Starting component B: | Pure-phase β-tricalcium phosphate, particle size <50 μm, 0.2 m$^2$/g BET surface area, 90% of the pores are in the diameter range 2 ± 1 μm and containing immobilised polymerisation activator |
| Starting component C: | Bifunctional monomer dianhydro-D-glucitol-bis[(oligo-L-lactyl methacrylate] (theoretically 2 L-lactic acid units per hydroxyl group of the dianhydro-D-glucitol) |
| Adhesion-imparting agent: | Methacrylic acid 2-hydroxyethyl ester (HEMA) |
| Thickener: | Dianhydro-D-glucitol-poly-D,L-lactide, $M_{th}$ = 17442 g/mol |

1. Preparation of Starting Component A:

1.706 g of dibenzoyl peroxide (phlegmatised with 25% by weight water) are dissolved in 15 ml of acetone. The resulting solution is mixed with 38.72 g of CERASORB (β-tricalcium phosphate, 0.2 m2/g, 90% of pore diameters being 2±1 μm). In the process, the CERASORB draws the solution up into the pore systems completely. After evaporating off the acetone, a flowable powder is obtained.

2. Preparation of Starting Component B:

1.280 g of N,N-bis(2-hydroxyethyl)-p-toluidine are dissolved in 15 ml of ethanol. The resulting solution is mixed with 38.72 g of CERASORB (β-tricalcium phosphate, 0.2 m$^2$/g, 90% of pore diameters being 2±1 μm). In the process, the CERASORB draws the solution up into the pore systems completely. After evaporating off the ethanol, a flowable powder is obtained.

3. Preparation of Starting Component C:

A mixture of 18.26 g (0.125 mol) of dianhydro-D-glucitol, 36.02 g (0.25 mol) of L-lactide and 220 mg of tin(II) 2-ethylhexanoate is stirred for 4 hours at 140° C., with exclusion of moisture. After cooling of the mixture to room temperature, a transparent tough solid is obtained which is dissolved in 120 ml of methylene chloride and then re-precipitated from. 1200 ml of heptane. The purified product is dissolved in 40 ml of methylene chloride. 50.6 g (0.5 mol) of triethylamine are added thereto. With ice-cooling, exclusion of moisture and stirring, 39.2 g (0.375 mol) of methacrylic acid chloride are carefully added dropwise. The reaction mixture is then allowed to warm up to room temperature, with stirring, and allowed to stand overnight at room temperature. The reaction mixture is then purified by means of extraction and dried over sodium sulphate, and 40 mg of p-methoxyphenol are added. The methylene chloride is drawn off in a vacuum rotary evaporator at a bath temperature of from 30 to 35° C. Subsequently, final traces of methylene chloride that still remain are removed using an oil pump vacuum. A light-yellow oil is obtained; yield:

m=38.7 g (54.3%)

IR (cm$^{-1}$): 3110 (vCH sp$^2$), 2994 (vCH sp$^3$) 2945 (vCH sp$^3$), 2879 (vCH sp$^3$), 1757 (C=O), 1722 (C=O), 1639 (C=C).

4. Preparation of the Self-Hardening, Bioabsorbable Composite Material:

From the starting components A and B, using starting component C, the self-hardening, bioabsorbable composite materials R1 to R4 were prepared (see Tab. 1). These have a processing time of from 2 to 10 minutes and they then cure within from 30 to 60 seconds.

The self-hardening, bioabsorbable composite materials were used to carry out adhesion tests using defatted cattle bones. For the purpose, square plates of bone (7×7×3 mm) were bonded to the middle of rectangular plates of bone (20×10×3 mm). After storage of the bonded bone plates in ambient air for 18 hours, the tensile shear strength was determined using a tensile testing machine from the Instron company. Furthermore, cylindrical test specimens (height 10 mm, diameter 10 mm) were prepared from the self-hardening, bioabsorbable composite materials using silicone rubber moulds. The compressive strength of those test specimens was likewise determined using a tensile testing machine from the Instron company (see Tab. 2).

TABLE 1

Composition of the self-hardening, bioabsorbable composite materials R1-4

| Formulation | Composition |
|---|---|
| R1 | 25.0% by weight of starting component A<br>25.0% by weight of starting component B<br>36.0% by weight of starting component C<br>9.0% by weight of adhesion-imparting agent<br>5.0% by weight of thickener |
| R2 | 27.5% by weight of starting component A<br>27.5% by weight of starting component B<br>32.4% by weight of starting component C<br>8.1% by weight of adhesion-imparting agent<br>4.5% by weight of thickener |
| R3 | 30.0% by weight of starting component A<br>30.0% by weight of starting component B<br>28.8% by weight of starting component C<br>7.2% by weight of adhesion-imparting agent<br>4.0% by weight of thickener |
| R4 | 30.0% by weight of starting component A<br>32.5% by weight of starting component B<br>25.2% by weight of starting component C<br>6.3% by weight of adhesion-imparting agent<br>3.5% by weight of thickener |

TABLE 2

Tensile shear strength of the plates of bone bonded using the self-hardening, bioabsorbable composite materials R1-4 and compressive strength of the test specimens prepared from R1-4.

| Formulation | Tensile shear strength [MPa] | Compressive strength [MPa] |
|---|---|---|
| R1 | 13.9 ± 8.1 | 74.4 ± 6.1 |
| R2 | 5.5 ± 2.6 | 78.1 ± 5.0 |
| R3 | 11.0 ± 2.8 | 83.9 ± 5.4 |
| R4 | 16.6 ± 8.3 | 79.1 ± 13.8 |

The invention claimed is:

1. Method of producing a self-hardening bioabsorbable composite material, wherein
   (i) a polymerisation initiator is immobilised with the aid of a first partial amount of an interconnectingly porous bioabsorbable inorganic bone regeneration material, (ii) a polymerisation activator is immobilised with the aid of a second partial amount of the bone regeneration material according to (i) or of a different interconnectingly porous bioabsorbable inorganic bone regeneration material, (iii) the components obtained in steps (i) and (ii) are mixed with a liquid or paste-form multi-functional monomer capable of polymerisation to form a biocompatible and bioabsorbable polymer or with a liquid or paste-form mixture of multi-functional monomers capable of polymerisation to form a biocompatible and bioabsorbable polymer, wherein at least one of the constituents mixed in is a water-soluble pore-forming substance which is added to the monomer, monomer mixture and/or the mixture thereof with the bone regeneration material in particulate form, and (iv) the monomer or monomer mixture contained in the mixture produced is polymerised and the composite material is obtained;

wherein calcium phosphate having a pore volume, accessible to the polymerisation initiator and/or the polymerisation activator, of 0.4 $cm^3/g$ or more, while retaining the integrity of the particles of the bone regeneration material and having the following characteristic data is used as the interconnectingly porous bioabsorbable inorganic bone regeneration material:

pore diameters from 0.1 to 500 μm;

particle sizes ($d_{50}$ values) of from 1 to 500 μm; and

BET surface area of at least 0.1 $m^2/g$;

and where the polymerization initiator and polymerization activator are contained in the pores of the porous bioabsorbable inorganic bone regeneration material.

2. Method according to claim 1, wherein in step (iii) one or more constituents which modify the properties of the monomer, monomer mixture and/or composite material are mixed in, which modifying constituents are selected from the group consisting of thickeners, diluents, polymeric fillers, porogens, pH-modifying substances, colourants, adhesion-imparting agents, and silicon compounds.

3. Method according to claim 1, wherein at least one of the constituents mixed in is a substance which alters the viscosity of the monomer, the monomer mixture and/or the mixture thereof with the bone regeneration material.

4. Method according to claim 3, wherein the substances altering the viscosity of the monomer, the monomer mixture and/or the mixture thereof with the bone regeneration material are oligomeric or polymeric derivatives of alpha-hydroxycarboxylic acids and/or are substances from the group of oligo- and poly-ethylene glycols.

5. Method according to claim 3, wherein dianhydro-D-glucitol-bis(poly-D,L-lactide) is used as viscosity-increasing substance.

6. Method according to claim 1, wherein at least one of the constituents mixed in is a substance which is water-soluble or which reacts with water to form water-soluble resultant products and which brings about a pH change in a water-containing medium.

7. Method according to claim 6, wherein sodium hydrogen carbonate is used as water-soluble pH-modifying and pore-forming substance.

8. Method according to claim 1, wherein at least one of the constituents mixed in is a substance which acts as an adhesion-imparting agent between the composite material and living hard tissue.

9. Method according to claim 8, wherein hydroxyl-group-containing adhesion-imparting agents are used as adhesion-imparting agent.

10. Method according to claim 1, wherein at least one of the constituents mixed in is a colourant or a contrast agent.

11. Method according to claim 1, wherein at least one of the constituents mixed in is a pharmaceutical active ingredient or an active ingredient mixture.

12. Method according to claim 11, wherein antibiotics, anti-inflammatories, growth factor proteins and/or cancerostatics are used as pharmaceutical active ingredients.

13. Method according to claim 1, wherein the first partial amount and the second partial amount of the bone regeneration material are used in a ratio of from 1:10 to 10:1 and/or the polymerisation initiator and the polymerisation activator are immobilised with the respective partial amounts of the bone regeneration material in a ratio of from 1:10 to 10:1 (based on weight in each case).

14. Method according to claim 1, wherein the bone regeneration material is used in the form of powder or granules.

15. Method according to claim 1, wherein in step (i) a solution of the polymerisation initiator is added to the bone regeneration material, the solution is allowed to infiltrate the bone regeneration material, and afterwards the bone regeneration material is dried.

16. Method according to claim 1, wherein a solution of the polymerisation initiator is mixed with the bone regeneration material in an amount of from 0.1 to 20% by weight (solid initiator based on bone regeneration material).

17. Method according to claim 1, wherein an organic peroxide is used as polymerisation initiator.

18. Method according to claim 1, wherein, in step (ii) a melt or solution of the polymerisation activator is added to the bone regeneration material, the solution is allowed to infiltrate the bone regeneration material, and afterwards the bone regeneration material is dried.

19. Method according to claim 1, wherein a solution of the polymerisation activator is mixed with the bone regeneration material in an amount of from 0.1 to 20% by weight (solid activator based on bone regeneration material).

20. Method according to claim 1, wherein one or more polymerisation activators are used which are selected from the group comprising N,N-bis(2-hydroxyethyl)-p-toluidine, N,N-dimethyl-p-toluidine, N,N-dimethyl-N,N-aniline, ascorbic acid and barbituric acid.

21. Method according to claim 1, wherein the polymerisation initiator is used in the form of a solution and/or the polymerisation activator is used in the form of a solution and the solution(s) is/are allowed to be drawn up by the bone regeneration material completely or as far as possible and the excess not drawn up is removed before step (iii).

22. Method according to claim 1, wherein inorganic bone regeneration material is selected from the group consisting of alpha-tricalcium phosphate, beta-tricalcium phosphate, octacalcium phosphate, calcium hydrogen phosphate, calcium orthophosphate and calcium pyrophosphate.

23. Method according to claim 1, wherein the same bone regeneration material is used for the immobilisation of the polymerisation initiator as for the immobilisation of the polymerisation activator.

24. Method according to claim 1, wherein the bone regeneration material for the immobilisation of the initiator and the bone regeneration material for the immobilisation of the activator differ from one another in their chemical and/or mineralogical nature.

25. Method according to claim 1, wherein calcium phosphate having the following characteristic data is used as the interconnectingly porous bone regeneration material:
pore diameters from 0.1 to 100 μm, and/or
particle sizes ($d_{50}$ values) of from 5 to 300 μm.

26. Method according to claim 1, wherein there is used calcium phosphate having a pore volume, accessible to the polymerisation initiator and/or the polymerisation activator, of from 0.4 to 3.3 cm$^3$/g, as the interconnectingly porous bone regeneration material, while retaining the integrity of the particles of the bone regeneration material.

27. Method according to claim 1, wherein the calcium phosphate bone regeneration material is used in crystalline, partly crystalline, glassy or amorphous form.

28. Method according to claim 1, wherein there is used, as the monomer or as monomers of the monomer mixture, a multi-functional oligomer having terminal methacrylate groups.

29. Method according to claim 4, wherein the oligomeric or polymeric derivatives of alpha-hydroxycarboxylic acids are lactic and/or glycolic acid.

30. Method according to claim 8, wherein methacrylic acid 2-hydroxyethyl ester is used as adhesion-imparting agent.

31. Method according to claim 1, wherein an organic peroxide selected from the group consisting of dibenzoyl peroxide, lauroyl peroxide and acetone is used as polymerisation initiator.

32. Method according to claim 1, wherein the monomer or monomers of the monomer mixture are selected from the group consisting of an oligomer of lactic acid, glycolic acid, delta-hydroxyvaleric acid, epsilon-hydroxycaproic acid, trimethylene carbonate and mixtures thereof.

* * * * *